United States Patent [19]
Hastings et al.

[11] Patent Number: 5,617,870
[45] Date of Patent: Apr. 8, 1997

[54] INTRAVASCULAR FLOW MEASUREMENT SYSTEM

[75] Inventors: Roger Hastings, Maple Grove; Paul Feld, Buffalo, both of Minn.

[73] Assignee: Scimed Life Systems, Inc., Maple Grove, Minn.

[21] Appl. No.: 304,565

[22] Filed: Sep. 12, 1994

Related U.S. Application Data

[63] Continuation-in-part of Ser. No. 55,702, Apr. 29, 1993, Pat. No. 5,346,508.

[51] Int. Cl.$^6$ .................................................... A61B 5/00
[52] U.S. Cl. ............................................. 128/692; 128/713
[58] Field of Search .................................. 128/691, 692, 128/713; 607/99; 606/27–31; 604/96

[56] References Cited

U.S. PATENT DOCUMENTS

| | | | |
|---|---|---|---|
| 3,075,515 | 1/1963 | Richards | 128/692 |
| 3,330,269 | 7/1967 | Pieper | 128/692 |
| 3,352,154 | 11/1967 | Djorup | 73/189 |
| 3,438,253 | 4/1969 | Kuether et al. | 73/204 |
| 3,789,831 | 2/1974 | Kopaniky et al. | 128/2.05 |
| 4,024,873 | 5/1977 | Antoshkiw et al. | 128/713 |
| 4,059,982 | 11/1977 | Bowman | 73/15 A |
| 4,217,910 | 8/1980 | Khalil | 128/692 |
| 4,685,470 | 8/1987 | Sekii et al. | 128/692 |
| 4,799,479 | 1/1989 | Spears | 128/303.1 |
| 4,920,697 | 5/1990 | Cottonaro et al. | 128/662.06 |
| 4,961,433 | 10/1990 | Christian | 128/772 |
| 5,002,059 | 3/1991 | Crowley et al. | 128/662.06 |
| 5,035,694 | 7/1991 | Kasprzyk et al. | 606/27 |
| 5,041,089 | 8/1991 | Mueller et al. | 604/96 |
| 5,078,717 | 1/1992 | Parins et al. | 606/48 |
| 5,094,246 | 3/1992 | Rusz et al. | 128/716 |
| 5,114,423 | 5/1992 | Kasprzyk et al. | 606/27 |
| 5,131,397 | 7/1992 | Crowley | 128/662.06 |
| 5,174,299 | 12/1992 | Nelson | 128/692 |
| 5,184,621 | 2/1993 | Vogel et al. | 128/642 |
| 5,373,850 | 12/1994 | Kohno et al. | 128/692 |
| 5,437,637 | 8/1995 | Lieber et al. | 128/692 |

FOREIGN PATENT DOCUMENTS

| | | | |
|---|---|---|---|
| WO91/03207 | 3/1991 | WIPO . | |
| 9117703 | 11/1991 | WIPO | 128/713 |
| WO92/00710 | 1/1992 | WIPO . | |
| WO92/22240 | 12/1992 | WIPO . | |

OTHER PUBLICATIONS

"Advantage of Peak Velocity Over Mean Measurments Made by Doppler Catheters", 3463, Scott J. Denardo, Lawrence Talbot, Victor Hargrave, Thomas A. Ports, Paul G. Yock, Supp I Cir, vol. 86, No. 4, Oct. 1992, I–870.

*Primary Examiner*—Angela D. Sykes
*Assistant Examiner*—Eric F. Winakur
*Attorney, Agent, or Firm*—Robert E. Atkinson

[57] ABSTRACT

A sensor coil is located on guidewire or perfusion catheter and introduced into the body. First the sensor coil is isolated from blood flow and used to make a set of static measurements. Next the sensor coil is heated in the presence of blood flow and a set of dynamic measurements are made which reflect the blood flow past the sensor coil.

3 Claims, 4 Drawing Sheets

INTRAVASCULAR FLOW MEASUREMENT SYSTEM

CROSS REFERENCE

This application is a continuation-in-part of parent application Ser. No. 08/055,702; filed Apr. 29, 1993; now U.S. Pat. No. 5,346,508; entitled, "Apparatus and Method for Performing Diagnostics and Intravascular Therapies", now allowed. The parent application is incorporated by reference herein in its entirety.

FIELD OF THE INVENTION

The present invention relates to an apparatus and a method for measuring blood flow inside of vessels within a patient's body.

BACKGROUND OF THE INVENTION

Several techniques are in use to measure the flow of blood within a patient's vasculature. Doppler ultrasound and dilution techniques can be used to study blood flow in vessels, and these devices are common. Hot wire anemometry has been proposed to measure blood flow as well.

The measurement of blood flow in a coronary artery is especially difficult due to the size and location of the vessel. For example, the measurement device must have a very small diameter so that the vessel under study is not occluded during the measurement. Occlusion will distort the flow measurement and can cause ischemia. It is also important that the flow measurement device generate a reproducible and accurate measure of blood flow as a function of time so that the pulsatile nature of the blood flow is revealed. Typically, this type of information is used by the physician to assess the efficacy of an angioplasty procedure.

The ideal flow measurement apparatus would be accurate, small, flexible and should have a sufficiently fast response time to track the pulsatile flow in the vessel. Both the cost and ease of use of the complete system needs to be considered as well to produce a commercially successful product. Presently available devices are not capable of simultaneously meeting these various requirements.

SUMMARY

The intravascular flow measurement system 16 of the present invention comprises a disposable flow measurement device 10 and a flow measurement calibration and display system 17. The flow measurement device 10 incorporates a single sensor coil 30 into an intravascular device such as a catheter or guidewire. In use the sensor coil 30 is introduced into the body and manipulated to the appropriate anatomic site. The sensor coil 30 is first calibrated then used to make the flow measurement. To calibrate the sensor coil 30 the physician retracts the sensor coil into the lumen 27 of a sheath 34 or the like to remove the sensor from the flow of blood. At this so called calibration site, the sensor coil 30 is used to measure body temperature. Next the sensor coil 30 is heated above ambient temperature and a quiescent current draw from the sensor coil 30 in this state is measured. This set of measurements is taken at the calibration site and they are referred to as the "static calibration measurements". After calibration the sensor coil 30 is advanced into the blood stream to a so called flow measurement site and heated. Preferably the sensor coil 30 is elevated to a fixed temperature difference over the non-flow temperature measurement. Next the amount of current required to maintain the sensor coil 30 at the specified temperature differential is measured. The instantaneous flow can be computed or inferred from the instantaneous current measurement. This set of measurements is taken at the measurement site and are referred to as the "dynamic measurements".

BRIEF DESCRIPTION OF THE DRAWINGS

An illustrative and exemplary intravascular flow measurement system 16 is shown throughout the figures. Throughout the several views like reference numerals indicate similar structures, in which.

DETAILED DESCRIPTION

Figure 1:
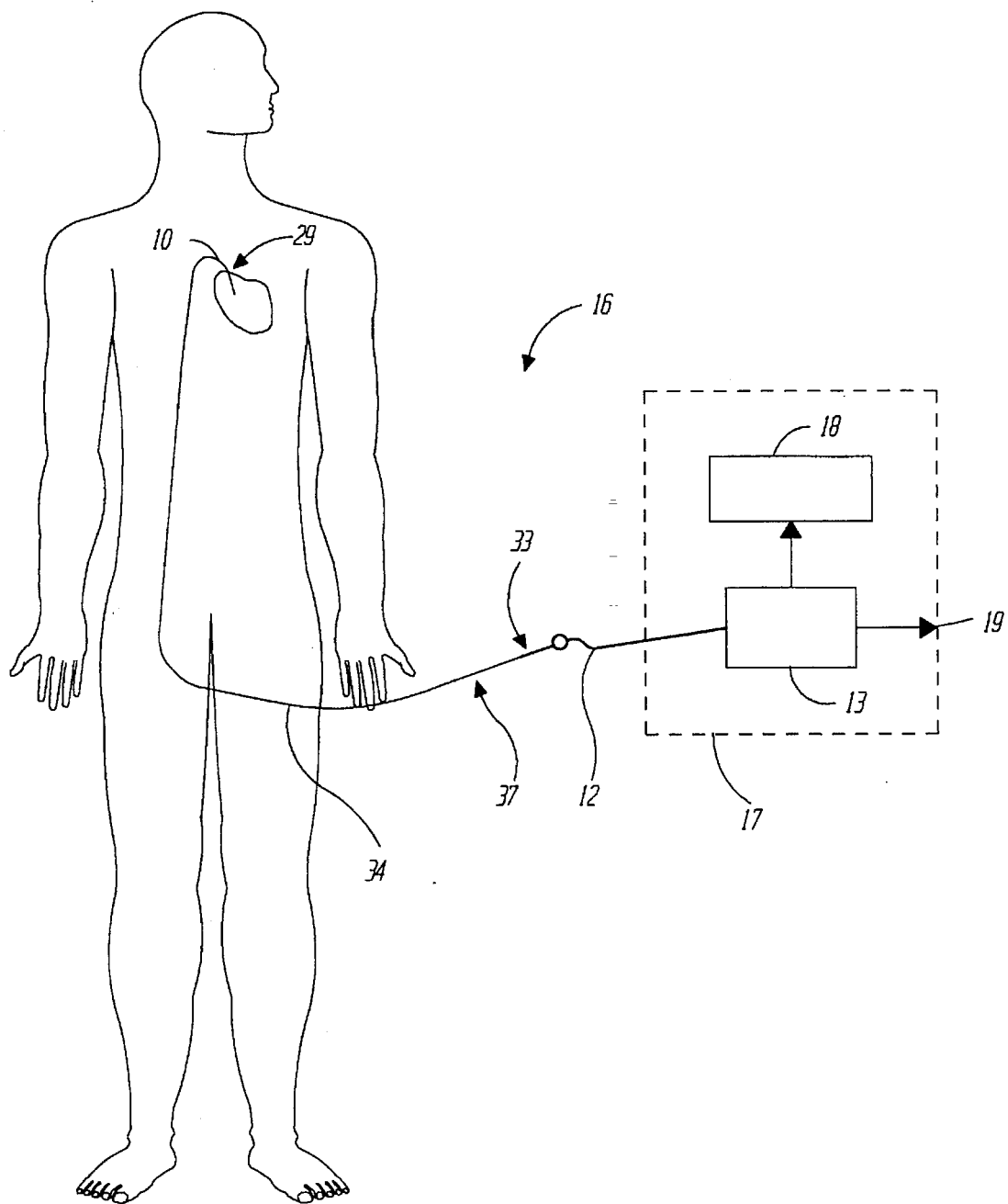
FIG. 1 is a schematic view of the system.

FIG. 1 shows an intravascular flow measurement system 16. The intravascular flow measurement device 10 is positioned in a coronary artery in the patient's body. The intravascular flow measurement device 10 has a distal end 29 and a proximal end 33. The intravascular flow measurement device 10 is located within a sheath 34 which has a distal end 29 and a proximal end 37. An appropriate cable 12 is used to couple the sensor coil 30 of the intravascular flow measurement device 10 to a calibration and display system 17. The calibration and display system 17 includes an electronic circuit 13 which is coupled to an output terminal 19 and a data display 18.

In this specific flow measurement situation the physician has passed the intravascular flow measurement device 10 through the guide catheter or sheath 34 to the desired anatomic site. Next the physician will manipulate proximal end 33 of the intravascular flow measurement device 10 to position both the sheath 34 and the sensor coil 30 with respect to the blood flow at this selected site. In use, the physician will manipulate the measurement device 10, the sheath 34, and several controls on the calibration and display system 17. Typically, the physician will observe the pulsatile blood flow on a laboratory monitor connected to output terminal 19, and observe averaged flow data on an appropriate data display 18 which is integrated into the calibration and display system 17.

Figure 2:
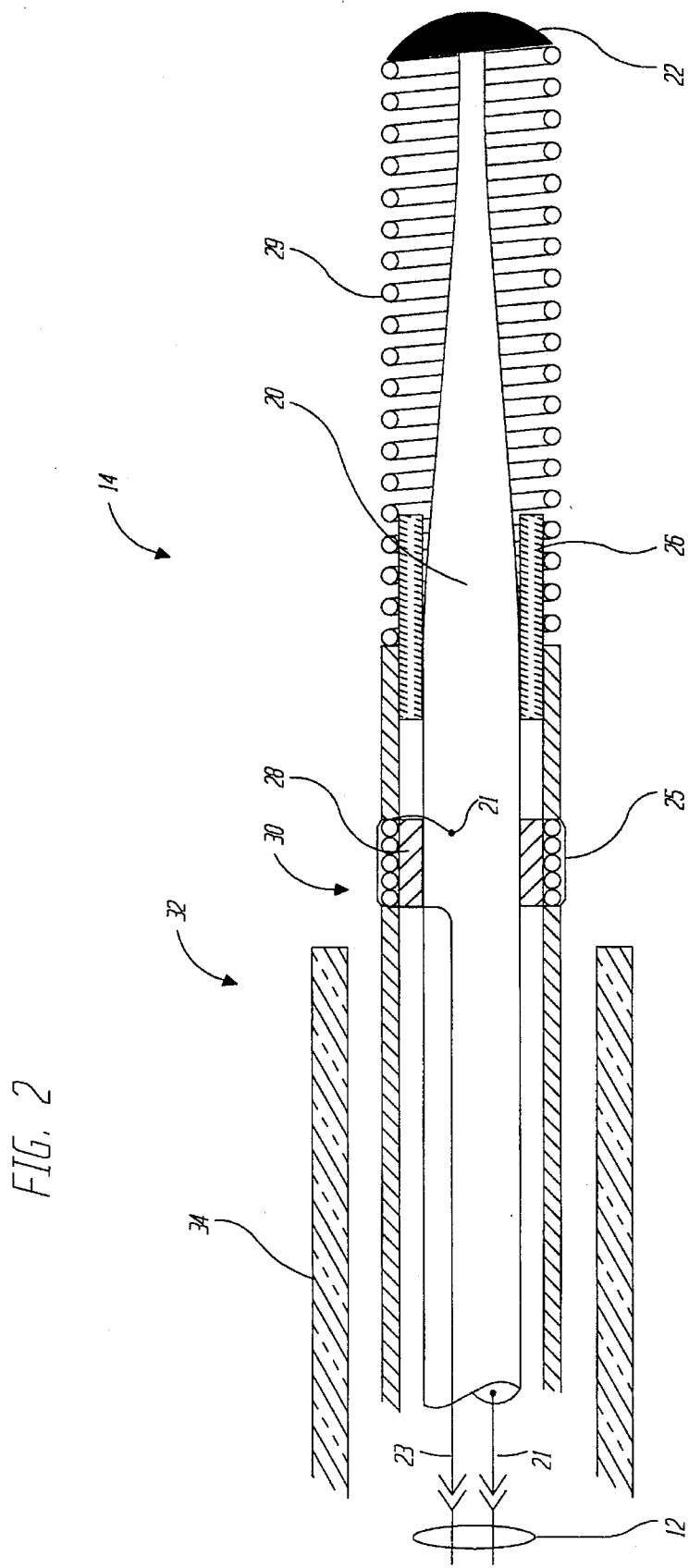
FIG. 2 is a guidewire incorporating the intravascular flow measurement device.

FIG. 2 shows an intravascular flow measurement device 10 incorporated into the distal end 29 of a guidewire 14. The guidewire 14 includes a wire core 20 which terminates in a distal tip 22. A spring coil 24 surrounds the wire core 20 and it is attached to both the distal tip 22 and to an anchor ring 26. The guide wire core 20 may be made of any appropriate material such as stainless steel. However to reduce the resistance of the electrical connections to the sensor coil 30 it is desirable to plate the wire core 20 with gold or silver to electrically couple to the sensor coil 30. The sensor coil 30 is mounted on an insulating spacer 28 which thermally and electrically isolates the sensor coil 30 from the wire core 20. The sensor coil 30 is preferably wound as a bifilar helix around the insulating spacer 28. One lead 21 of the sensor coil 30 is electrically connected to the plated surface of the wire core 20 while the other lead 23 extends from the proximal end of the guidewire 14. These two leads are connected via an appropriate cable 12 to the calibration and display system 17. A hydrophilic slip coat or silicone slip coat 25 is applied onto the exterior of the guidewire to facilitate use of the wire. Coatings of this type prevent blood from coagulating on the sensor coil 30. These coating are also an aid to repositioning the measurement device 10 both within the lumen 27 of the sheath 34 and within the vasculature.

In the figure, the sensor coil 30 is shown proximate the distal end 32 of a guide catheter or therapy selection sheath 34. In use, the physician retracts the sensor coil 30 a short distance into the lumen 27 of the sheath 34. Temperature and quiescent current measurements are made at this calibration site. Next the sensor coil 30 is advanced out of the sheath 34 to a measurement site where it is exposed to blood flow and the dynamic flow measurements are made.

Figure 3:
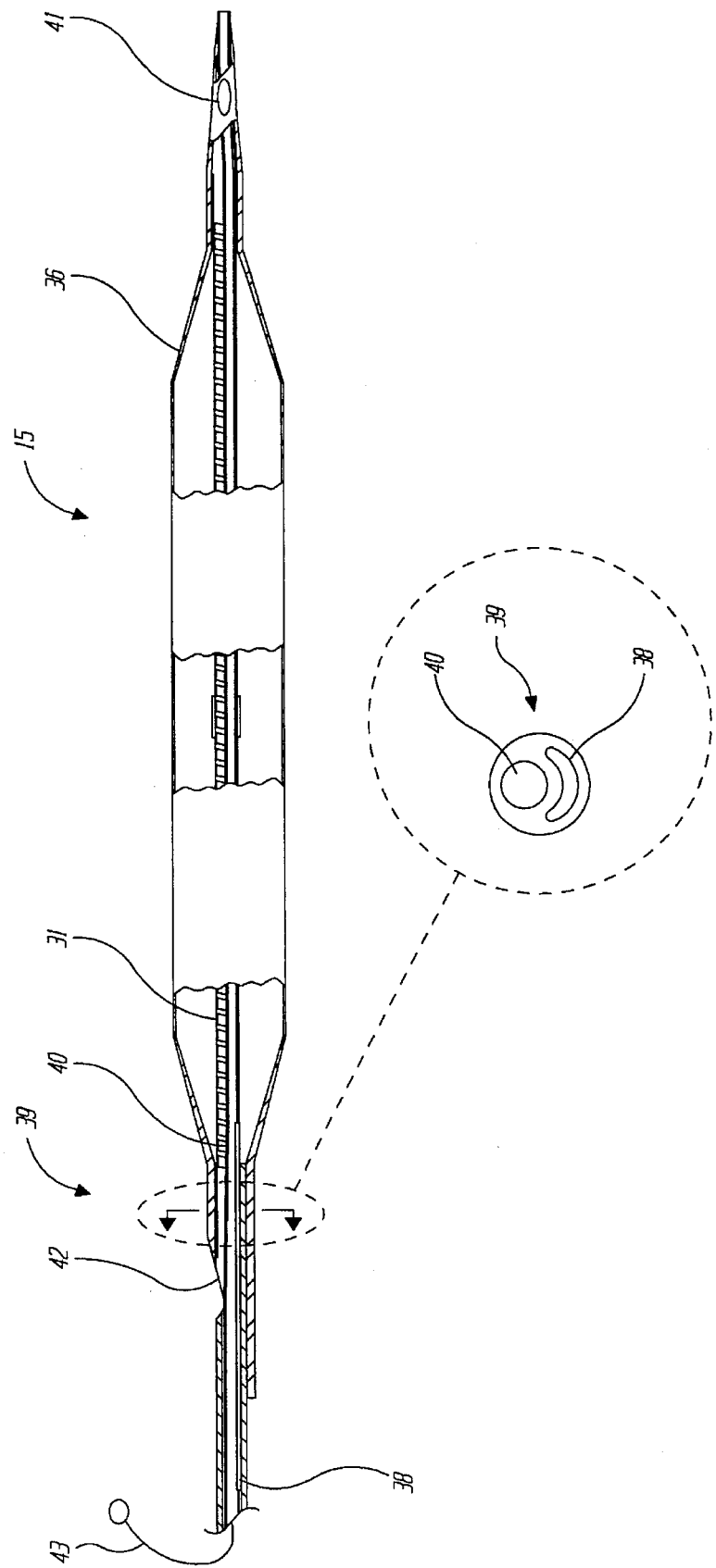
FIG. 3 is a perfusion catheter incorporating the intravascular flow measurement device.

FIG. 3 shows an intravascular flow measurement device 10 incorporated into a perfusion catheter 15. This particular perfusion catheter 15 includes a balloon 36. The perfusion catheter body 39 is generally circular in cross section with several lumens. The balloon 36 can be inflated by injecting fluid into an inflation lumen 38. After inflation the patient's blood vessel is perfused by the blood flowing through the main lumen 40 of the perfusion catheter 15. Blood enters the main lumen 40 through an inlet aperture 42 and then exits through apertures in the distal tip 41 of the perfusion catheter 15. A sensor coil 31 is located on the interior wall of the main lumen 40. Consequently the blood flowing through the main lumen 40 contacts the sensor coil 31 and can be measured with the sensor coil 31. The sensor coil 31 is electrically connected to the calibration and display system 17 through a suitable set of wires shown as cable 43. To calibrate this sensor coil 31 the perfusion catheter 15 is introduced through a sheath or the like and the static temperature and the quiescent current "Io" measurements are made before the balloon 36 is deployed and inflated. Since the diameter of the central lumen 40 is known, the blood flow velocity measurement can be used to measure the mass flow rate of blood in the artery which may prove desirable in many clinical settings. In either form of intravascular flow velocity measurement device the dynamic measurements are made by heating the sensor coil above the ambient blood temperature and monitoring the current draw of the sensor coil 30. Suitable computation and control measurements are made and the resulting instantaneous flow velocity is available as a numeric value on a suitable data display 18 or available through output terminal 19 to a suitable real time analog display (not shown).

Figure 4:
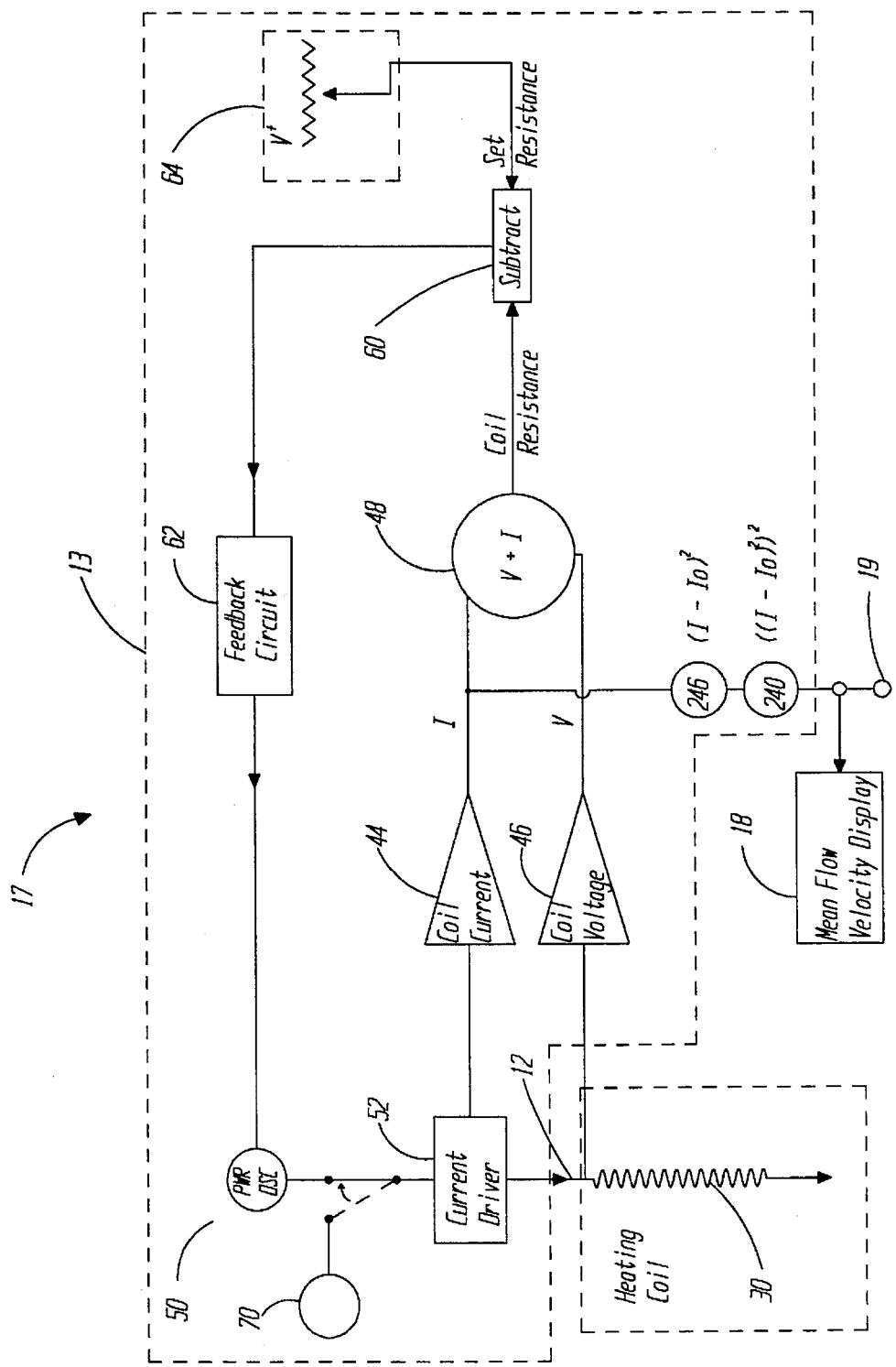
FIG. 4 is a schematic diagram of a representative implementation of the flow measurement system.

FIG. 4 shows an illustrative circuit for carrying out a flow velocity measurement with the intravascular flow velocity measurement device 10 shown in either FIG. 2 or FIG. 3. It should be appreciated that the intravascular flow velocity measurement system 16 can be partitioned in a number of ways and the exemplary system described can be modified in various ways without departing from the scope of the invention. One exemplary partitioning of functions would rely on digital devices to perform the calculation functions shown in block 46. A brief description of the flow measurement process facilities and understanding of this block schematic diagram.

In general the flow velocity measurement is derived from a measurement of the current required to maintain the temperature of the sensor coil above the ambient temperature at the measurement site. Expressed as an equation the velocity "v" is given by $v=c(I-I_o)^4$, where "I" is the measured current required to elevate the temperature of the sensor coil 30 in the presence of blood flow. The value of the quiescent current to maintain the temperature elevation in the no flow condition is represented by "Io".

The conversion constant "c" appears to depend strongly on the physical characteristics of the sensor coil 30 and the related insulating spacer 28 and device structure. Conventional manufacturing techniques are sufficient to produce intravascular measurement devices 10 with similar values of the constant "c". It is not expected that the calibration and display system 17 will have to accommodate devices with widely varying values of "c". The dimensionless constant "c" also varies with the thermal properties of the fluid. Testing has shown that "c" does not vary appreciably with hematocrit in mammalian blood.

The set of calibration measurements includes measurement of ambient temperature at or near the flow measurement site in still blood at a so called calibration site. In the present system the sensor coil 30 is interrogated with a small current to determine the resistance of the sensor coil. The sensor coil is coupled to the calibration and display system via sensor coil leads 21, 23 which have a characteristic resistance. In general it is desirable to minimize the lead resistance. The preferred sensor coil material is selected based upon the lead resistance with silver, platinum, and nickel iron alloy being useful depending on lead resistance. Each of these sensor coil materials exhibits a resistance that is a linear function of temperature. The current level and duration of the interrogation pulses does not materially raise the temperature of the sensor coil. This measurement may be made with an AC current or a DC current.

The measured blood temperature is used as a base for a temperature difference setpoint. The preferred temperature difference is 5 degrees or less. This temperature differential can be adjusted by the physician if desired. A feedback system drives the sensor coil to the desired temperature and maintains it at that temperature. Although both linear and non-linear feedback can be used, the preferred feedback scheme is non-linear. It is desireable to rapidly approach the setpoint temperature to maintain high dynamic range but it is also important not to overshoot the target temperature and potentially injure the blood. It is undesirable to overheat the sensor coil 30 in the vessel and yet flow induced cooling must be quickly overcome to make pulsatile measurements.

Turning to the schematic diagram of FIG. 4 an exemplary calibration and display system 17 is shown in block form. In the measurement mode, the oscillator 50 generates pulses which are used by current driver 52 to drive current through the sensor coil 30 or sensor coil 31. The current through the sensor coil and the voltage across the sensor coil are available in analog form through operational amplifiers 44 and 46. A divider 48 forms the quotient of the two values generating a coil resistance measurement. The subtractor circuit 60 and feedback circuit 62 together alter the pulse width or duty cycle of the oscillator 50. Thus in operation the duty cycle of the oscillator 50 reflects the current draw of the coil required to maintain the constant temperature differential. The instantaneous current through the sensor coil 30 is related to the flow velocity. In practice the displayed flow value at data display 18 is the instantaneous coil current "I" is raised to the fourth power, as represented by blocks 46 and 47. This value is proportional to flow velocity and it is delivered to the output terminal 19. This sharp dependance of flow measurement on measured current makes the in situ calibration important especially for quantitative measurements.

In the calibration mode the sensor coil is withdrawn into a sheath to the calibration position for a static blood temperature measurement. Switch 68 is used to couple the low current source 70 to the sensor coil 30. This current driver is set to deliver low current pulses to interrogate the sensor coil to determine body temperature at the calibration site. Although switch 68 may be used to select a separate low duty cycle current source 70 to generate the required interrogation current, other current sources may be substituted. The coil resistance measurement during the calibration process is monitored and used to set the value of resistor divider 64. This potentiometer sets the target temperature of the dynamic measurement. During the dynamic measurement mode the current driver 52 is enabled to produce higher current pulses to drive the coil 30 to a higher setpoint temperature.

Having thus described the intravascular flow measurement system 16 and the method for using it should be apparent that many changes can be made to the system without departing from the scope of the invention.

What is claimed is:

1. An intravascular flow measurement device comprising:

an elongate perfusion body having a distal end, a proximal end, and a main lumen, said main lumen having an interior wall;

a sensor coil located on the interior wall of said main lumen;

an inlet aperture proximal to said sensor coil, communicating with said main lumen; and an outlet aperture distal to said sensor coil, communicating with said main lumen.

2. The intravascular flow measurement device of claim 1 further comprising:

a balloon located distal to said inlet aperture and coupled to the said perfusion body.

3. The intravascular flow measurement device of claim 2 further comprising:

a balloon inflation lumen located in said perfusion body, for coupling inflation fluid to said balloon.

\* \* \* \* \*

UNITED STATES PATENT AND TRADEMARK OFFICE
CERTIFICATE OF CORRECTION

PATENT NO. : 5,617,870
DATED : April 8, 1997
INVENTOR(S) : HASTINGS et al.

It is certified that error appears in the above-identified patent and that said Letters Patent is hereby corrected as shown below:

ON THE TITLE PAGE:

On page 1, at References Cited, U.S. PATENT DOCUMENTS, line 11, "4,920,697" should be --4,920,967--.

In column 1, at lines 8-9, delete ", now allowed".

In column 6, claim 2, line 4, delete "the".

Signed and Sealed this

Twenty-second Day of December, 1998

Attest:

BRUCE LEHMAN

*Attesting Officer*       Commissioner of Patents and Trademarks